United States Patent [19]

Weis et al.

[11] Patent Number: 4,939,285

[45] Date of Patent: Jul. 3, 1990

[54] PROCESS FOR THE PREPARATION OF METAL SALTS OF PHOSPHORIC AND PHOSPHONIC ACID ESTERS

[75] Inventors: Claus D. Weis, Pfeffingen; Peter Sutter, Muttenz, both of Switzerland

[73] Assignee: Ciba-Geigy Corporation, Ardsley, N.Y.

[21] Appl. No.: 215,845

[22] Filed: Jul. 6, 1988

[30] Foreign Application Priority Data

Jul. 13, 1987 [CH] Switzerland ............................ 2657/87
Feb. 19, 1988 [CH] Switzerland ............................. 634/88

[51] Int. Cl.$^5$ ............................. C07F 9/09; C07F 9/38
[52] U.S. Cl. ...................................... 558/214; 556/19; 556/24; 558/131
[58] Field of Search ................... 558/131, 214; 556/19, 556/24

[56] References Cited

U.S. PATENT DOCUMENTS 3,064,031 11/1962 Zimmerer ............................ 558/131
4,233,198 11/1980 Nölken ................................ 260/29.6
4,251,492 2/1981 Marshall ............................. 423/226

FOREIGN PATENT DOCUMENTS 245207 11/1987 European Pat. Off. .
2160730 6/1972 Fed. Rep. of Germany .

OTHER PUBLICATIONS

H. Crisitol, M. Levy and C. Marty, J. Organometal Chemical Abstract, vol. 12 (1968) 459-470.
M. Brauninger, W. Schwarz. A. Schmidt; Zeitschrift Für Naturforschung, vol. B. 34B, 1703(1979).
Bulletin De La Societe Chemique De France (1975), pp. 2083-2088.
Journal of General Chem. of the USSR, vol. 50 (1980), pp. 31-34.

Primary Examiner—Anton H. Sutto
Attorney, Agent, or Firm—Kevin T. Mansfield; Edward McC. Roberts

[57] ABSTRACT

Metal salts of phosphoric and phosphonic acid esters of formula

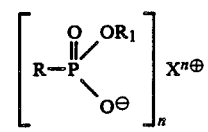

(1)

wherein
R is $C_1$-$C_4$ alkoxy or straight chain or branched unsubstituted $C_1$-$C_{20}$ alkyl or $C_2$-$C_6$ alkenyl,
$R_1$ is hydrogen or $C_1$-$C_4$ alkyl,
X is a metal cation, and
n is an integer from 1 to 3 corresponding to the valence of X, are prepared by reacting n moles of a phosphoric or phosphonic acid or an ester thereof, of formula

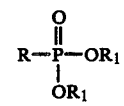

(2)

wherein R, $R_1$ and n are as defined above, with 1 mole of a metal $X^n$, if desired with cooling. These salts can be used, for example, as flame retardants, fertilizers or emulsifiers for aqueous plastics dispersions.

6 Claims, No Drawings

PROCESS FOR THE PREPARATION OF METAL SALTS OF PHOSPHORIC AND PHOSPHONIC ACID ESTERS

The present invention relates to a novel process for the preparation of metal salts of phosphoric and phosphonic acid esters.

The preparation of the sodium salt of monomethyl methylphosphonate by partial alkaline hydrolysis of dimethyl methylphosphonate in water, or a mixture of dioxane/water, with aqueous sodium hydroxide has been described by H. Cristol, M. Levy and C. Marty in J. Organometallic Chem. 12, 459 (1968).

The preparation of metal salts of monomethyl methylphosphonate by reaction of dimethyl methylphosphonate (DMMP) with the appropriate metal halides is disclosed in European patent application No. 0 245 207. It is not possible to prepare the alkali salts by this process, because the alkali metal halides, for example lithium, sodium or potassium chloride or the corresponding bromides, do not react with dimethyl methylphosphonate.

The preparation of the alkali metal salts from phosphoric acid ester chloride and potassium hydroxide is described by M. Bräuninger, W. Schwarz, A. Schmidt, Zeitschrift für Naturforschung B, 34B, 1703 (1979); and the reaction of disphosphorous pentoxide with methanol and subsequent treatment of the reaction product with potassium salts is disclosed in German Offenlegungsschrift 2 160 730.

A process has now been found in which mono- to trivalent salts of phosphonic acid esters can be prepared in simple manner.

The process of this invention for the preparation of metal salts of phosphoric and phosphonic acid esters of formula

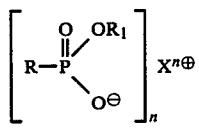
(1)

wherein
R is $C_1-C_4$alkoxy or straight chain or branched unsubstituted $C_1-C_{20}$alkyl or $C_2-C_6$alkenyl,
$R_1$ is hydrogen or $C_1-C_4$alkyl,
X is a metal cation, and
n is an integer from 1 to 3 corresponding to the valence of X,
comprises reacting n moles of a phosphoric or phosphonic acid or an ester thereof, of formula

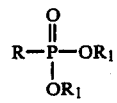
(2)

wherein R, $R_1$ and n are as defined above, with 1 mole of a metal $X^n$, if desired with cooling.

The reaction with the metal is carried out in a temperature range from 20° to 200° C., preferably from 25° to 180° C.

Suitable metals are those of groups Ia, IIa, IIb, IIIa, IVa and VIII of the Periodic Table, and are preferably lithium, sodium, potassium, magnesium, calcium, zinc, tin, iron, cobalt and aluminum.

A preferred process comprises reacting n moles of a phosphonic acid ester of formula

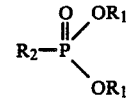

wherein $R_2$ is $C_1-C_4$alkoxy and $R_1$ is $C_1-C_4$alkyl, with 1 mole of a metal $X^n$ of groups Ia and IIa of the Periodic Table.

The most preferred process comprises reacting n moles of a phosphonic acid ester of formula

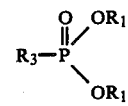

wherein $R_3$ is $C_1-C_{10}$alkyl and $R_1$ is $C_1-C_4$alkyl, with 1 mole of a metal $X^n$ selected from groups Ia, IIa, IIb, IIIa, IVa and VIII of the Periodic Table.

The reaction proceeds in accordance with the scheme

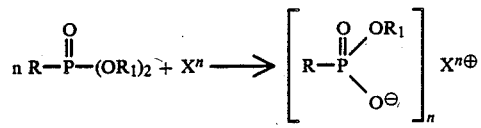

in the course of which carbon monoxide, methane, ethylene, ethane and lower dialkyl ethers are formed as by-products, depending on the phosphate or phosphonate employed. All these gaseous products can be incinerated or oxidised in an environmentally safe manner. From the ecological aspect, this feature represents an advance over the reaction of European patent application No. 0 245 207, which always results in the formation of an alkyl chloride that must either be incinerated (with subsequent formation of hydrogen chloride) or condensed.

The reaction of this invention is partially exothermic, so that appropriate cooling must be ensured. This problem can also be dealt with by carrying out the reaction in an excess of the phosphonate employed.

The lithium salt obtained by the process is novel and constitutes a further object of the invention.

With alkali metals, the reaction proceeds in a much shorter time than with other metals. The reaction time thus varies within wide limits. In can be, for example, from a few minutes to several days, in particular from 30 minutes to 5 days, for example from 30 minutes to 3 days.

The metal salts of formula (1), wherein R is $C_1-C_4$alkoxy and $R_1$ is $C_1-C_4$alkyl, can be used as fertilisers (q.v. for example German Offenlegungsschrift No. 2 160 730).

Metal salts of formula (1), wherein R is straight chain or branched unsubstituted $C_6-C_{20}$alkyl and $R_1$ is $C_1-C_4$alkyl, are useful emulsifiers for aqueous plastics dispersions (q.v. for example U.S. Pat. No. 4 233 198), and those wherein R and $R_1$ are $C_1-C_4$alkyl can be used as flame retardants, for example by blending them with the plastics material to be protected and fusing the mixture to a homogeneous melt in the temperature range from 200°–420° C. They can, however, also be used for flameproofing wood by impregnating the wood with an aqueous or organic solution containing these salts.

Alkali metal salts of formula (1), wherein R is $C_1$-$C_7$alkyl and $R_1$ is hydrogen, methyl or ethyl, are disclosed in U.S. Pat. No. 4 251 492. These salts are used as complexing agents in solutions for removing $H_2S$ from gases or liquid hydrocarbons.

The process of this invention is illustrated by the following Examples in which percentages are by weight, unless otherwise stated.

EXAMPLE 1

0.35 g of lithium are suspended in 50 ml of dimethyl methylphosphonate (hereinafter abbreviated to DMMP), and the suspension is heated to 125°–130° C. over 15 minutes. The heating means is removed at this temperature and the lithium goes into solution, accompanied by evolution of heat and a rise in temperature to 150°–155° C., whereupon a white suspension forms. The temperature is kept for 30 minutes at 155° C. and excess DMMP is thereafter removed by distillation. The precipitated lithium salt is stirred in 120 ml of acetone, isolated by filtration, washed with 50 ml of diethyl ether and dried under vacuum at 90° C., affording 5.4 g (93% of theory) of the salt of formula

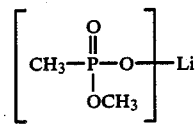

which melts at >300° C.

EXAMPLE 2

Under nitrogen, 7.67 g of sodium are added to 300 ml of DMMP heated to 100° C. Upon completion of the reaction, the mobile suspension is stirred for 30 minutes at 150° C. and excess DMMP is removed by distillation. The crystalline residue is stirred in 100 ml of acetone, isolated by filtration and washed with 50 ml of acetone and 50 ml of diethyl ether. Yield: 42.5 g (96.5% of theory) of the salt of formula

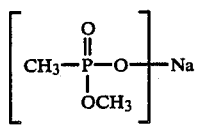

which melts at >300° C.

EXAMPLE 3

13 g of potassium are added, in portions, to 300 ml of DMMP heated to 70° C. Upon completion of the addition, the mixture is stirred for 1 hour and excess DMMP is then removed by distillation. The white crystalline residue is stirred in 100 ml of acetone, isolated by filtration and washed with 70 ml of acetone. Yield: 48.1 g (97.5% of theory) of the salt of formula

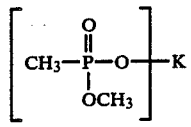

in the form of hygroscopic crystals with a melting point of 211°–213° C.

EXAMPLE 4

With stirring, 0.35 g of lithium are suspended in 38 g of diethyl methylphosphonate, the temperture rising to 120° C. in the course of the ensuing exothermic reaction. The resultant suspension is heated for 30 minutes to 140° C. After cooling, 100 ml of acetone are added to the suspension. The precipitated salt is isolated by filtration, washed with 50 ml of acetone and 50 ml of diethyl ether, and dried, affording 5.8 g (98% of theory) of the salt of formula

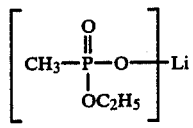

which melts at >350° C.

EXAMPLE 5

With stirring, 0.7 g of lithium are suspended in 83 g of diethyl ethylphosphonate, the temperature rising to 120° C. in the course of the ensuing exothermic reaction. The resultant suspension is heated for 30 minutes to 140° C. After cooling, 100 ml of acetone are added to the suspension. The precipitated salt is isolated by filtration, washed with 50 ml of acetone and 50 ml of diethyl ether, and dried, affording 13.15 g (91% of theory) of the salt of formula

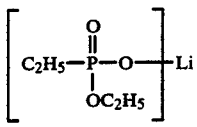

which melts at >300° C.

EXAMPLE 6

With stirring, 24.3 g of magnesium turnings are heated to the boil in 600 ml of DMMP. As soon as the reaction of the metal with the DMMP commences, the heating means is removed and the reaction proceeds of its own accord. As soon as the vigorous reaction has subsided (ca. 20–30 minutes), the reaction mixture is heated for 1½ hours. After cooling, the solution separates into two layers. The upper phase is removed by suction, and the lower, viscous phase is stirred in 250 ml of acetone. Stirring is then continued for 12 hours in order to obtain, by slow crystallisation, a readily filterable, granular product. The crystals are stirred in 500 ml of acetone for 2 hours, isolated by filtration, and washed with 150 ml of acetone and 150 ml of diethyl ether. Yield: 230 g (95% of theory) of the salt of formula

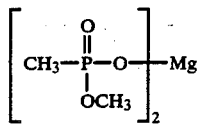

in the form of white crystals with a melting point of 127° C.

EXAMPLE 7

2.43 g of magnesium are suspended in 76 g of diethyl methylphosphonate and the suspension is heated to 180° C., whereupon reaction commences. After 1 hour, the viscous solution obtained is poured out while still hot and stirred in 200 ml of acetone. The viscous residue is then concentrated by evaporation under vacuum at 100° C., affording 26.1 g of a glassy residue of formula

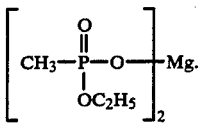

EXAMPLE 8

20 g of calcium are suspended in 500 ml of DMMP and the suspension is heated to reflux. Reaction commences at 170° C., accompanied by evolution of gas. The clear solution obtained after 70 hours is concentrated on a rotary evaporator until 200 ml of a viscous residue are obtained. This residue is stirred in 300 ml of acetone, and the crystalline slurry obtained after 30 minutes is filtered. The filter product is washed with 200 ml of acetone and 200 ml of diethyl ether and dried, affording 130.5 g (100% of theory) of the salt of formula

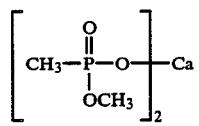

which melts at >300° C.

EXAMPLE 9

The procedure of Example 8 is repeated, using 4.0 g of calcium and 76 g of diethyl methylphosphonate, to give 28 g (99% of theory) of the salt of formula

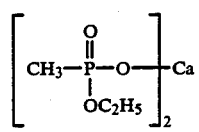

which melts at >300° C. (dec.).

EXAMPLE 10

5 g of cobalt powder are heated to the boil in 120 ml of DMMP for 4 days. The blue solution is then filtered hot to remove undissolved metal. The filtrate is cooled, giving blue crystals which are isolated by filtration after 24 hours and washed with diethyl ether and dried, affording 1.93 g (8% of theory) of the salt of formula

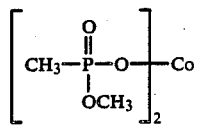

with a melting point of 133°–136° C.

EXAMPLE 11

With stirring, 25 g of iron powder are heated to the boil in 500 ml of DMMP for 3 days. The solution is then filtered, under nitrogen, to remove undissovled iron (21.6 g ), and the filtrate is evaporated to dryness under vacuum at 15.6 mbar. The white precipitate is isolated by filtration and dried, affording 16.0 g (78%, based on the iron consumed) of the salt of formula

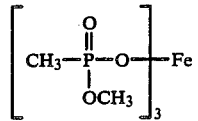

which melts at >300° C. (dec.).

EXAMPLE 12

5 g of tin powder are heated to reflux in 100 ml of DMMP for 3 days. The solution is then filtered hot and the filtrate is concentrated on a rotary evaporator (90° C./13 mbar) to give a red oil which crystallises on cooling. The crystalline residue is washed with 30 ml of acetone and dried, affording 12.5 g (89% of theory) of the salt of formula

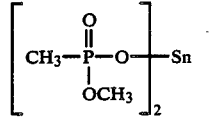

as a white powder which melts at >300° C.

EXAMPLE 13

With stirring, 1.08 g of aluminium foil are heated vigorously to reflux in 50 ml of DMMP in the presence of 10 mg of magnesium. A further 10 mg of magnesium are added each time after 1½, 6 and 24 hours. The total reflux time is 48 hours. The white suspension is then evaporated to dryness. The residue is washed in succession with 100 ml of methanol and 100 ml of water and then stirred for 20 minutes. The precipitate is isolated by filtration and washed on the filter in succession with water (10 ml) and methanol (10 ml), and subsequently dried under vacuum at 120° C., affording 13.4 g (94% of theory) of the salt of formula

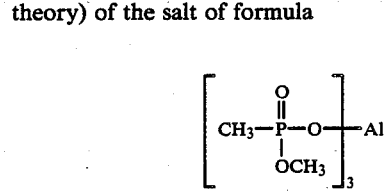

which melts at >300° C.

EXAMPLE 14

0.7 g of lithium are added, under nitrogen, to 112 g of trimethyl phosphate. The mixture is then heated for 30 minutes to 180° C. and this temperature is kept for a further 2 hours. The clear solution is evaporated to dryness on a rotary evaporator at 18.2 mbar and at a bath temperature of 90° C. The white residue is stirred for 1 hour in 80 ml of acetone and then isolated by filtration using a glass filter funnel. The filter residue is washed first with 30 ml of acetone, then with 50 ml of diethyl ether, and subsequently dried under vacuum at 90° C., affording 11.5 g (87% of theory) of the salt of formula

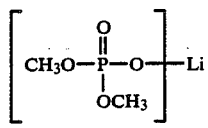

in the form of white crystals which melt at >300° C.

EXAMPLE 15

2.3 g of sodium are added, in small portions, under nitrogen and over 5 minutes to 112 g of trimethyl phosphate preheated to 120° C. The temperature slowly rises to 160° C. The suspension is the stirred for 2 hours at 200° C. and subsequently the clear, colourless solution is evaporated to dryness on a rotary evaporator under reduced pressure (18.2 mbar) at a bath temperature of 90° C. The white residue is stirred in 80 ml of acetone for 15 minutes and then isolated by filtration using a glass filter funnel. The filter residue is washed first with 30 ml of acetone and then with 50 ml of diethyl ether and dried under vacuum at 90° C., affording 13.9 g (100% of theory) of the salt of formula

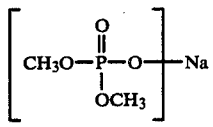

in the form of white crystals which melt at 242°-243° C.

EXAMPLE 16

A total amount of 3.9 g of potassium is added, in small portions, under nitrogen over 25 minutes to 112 g of trimethyl phosphate preheated to 100° C. The suspension is then stirred for 2 hours at 170°-180° C. The clear, colourless solution is evaporated to dryness on a rotary evaporator under reduced pressure (18.2 mbar) at a bath temperature of 90° C. The white crystalline residue is stirred for 15 minutes in 80 ml of acetone and then isoalted by filtration using a glass filter funnel. The filter residue is washed first with 30 ml of acetone and then with 50 ml of diethyl ether and dried under vacuum at 90° C., affording 48.1 g (97.5% of theory) of the salt of formula

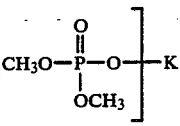

in the form of very hygroscopic crystals which melt at 166°-168° C.

EXAMPLE 17

Obeche wood shingles 115 m long, 20 mm wide and 3 mm thick are immersed at a liquor ratio of 1:5 (weight of wood:weight of liquor) for 60 minutes at 20° C. in a 7.5% by weight aqueous solution of the compound of formula

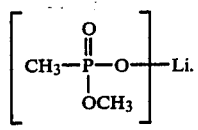

After impregnation, the shingles are hung to dry in the air for 16 hours and tested for their flame resistance by placing them vertically in a combustion chamber, igniting them for 3 and 6 seconds, and measuring the further combustion time in seconds.

For comparison purposes, a simultaneous test is carried out with a hot liquor of 90° C. which does not contain a compound of the above formula (immersion time: 30 minutes). The percentage concentration of active substance to be tested in calculated from the liquor pick-up. The results are reported in Table I.

TABLE I

| Liquor concentration | Liquor temperature | Impregnation time in minutes | Pick-up | Concentration of active substance in % | Flame resistance ignition time | |
|---|---|---|---|---|---|---|
| | | | | | 3 sec | 6 sec |
| 0% | 90° C. | 30 | 71% | — | burns | burns |
| 7.5% | 20° C. | 60 | 47% | 3.5% | 0 sec | 0 sec |

EXAMPLE 18

The procedure of Example 17 is repeated, except that impregnation is effected for 30 minutes with a hot liquor of 90° C. The results are reported in Table II.

TABLE II

| Liquor concentration | Liquor temperature | Impregnation time in minutes | Pick-up | Concentration of active substance in % | Flame resistance ignition time | |
|---|---|---|---|---|---|---|
| | | | | | 3 sec | 6 sec |
| 0% | 90° C. | 30 | 71% | — | burns | burns |
| 7.5% | 90° C. | 30 | 71% | 5.3% | 0 sec | 0 sec |

What is claimed is:
1. The metal salt of formula

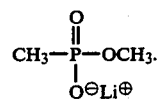

2. A process for the preparation of a metal salt of a phosphoric or phosphonic acid ester of formula

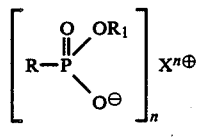

(1)

wherein
R is $C_1$–$C_4$alkoxy or straight chain or branched unsubstituted $C_1$–$C_{20}$alkyl or $C_2$–$C_6$alkenyl,
$R_1$ is $C_1$–$C_4$alkyl,
X is the cation of a metal of groups Ia, IIa, IIb, IIIa, IVa or VIII of the periodic table,
n is an integer from 1 to 3 corresponding to the valence of X, which process comprises reacting at a temperature of from 20° to 200° C. n moles of an ester of formula

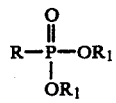

(2)

wherein R, $R_1$ and n are as defined above, with 1 mole of a metal $X^n$, if desired with cooling.

3. A process according to claim 2, wherein X is the cation of lithium, sodium, potassium, magnesium, calcium, zinc, tin, iron, cobalt or aluminium.

4. A process according to claim 3, wherein the reaction is carried out in the temperature range from 25° to 180° C.

5. A process according to claim 2, which comprises reacting n moles of a phosphoric acid ester of formula

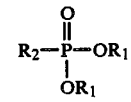

wherein $R_2$ is $C_1$–$C_4$alkoxy and $R_1$ is $C_1$–$C_4$alkyl, with 1 mole of a metal $X^n$ selected from groups Ia and IIa of the Periodic Table.

6. A process according to claim 2, which comprises reacting n moles of a phosphonic acid ester of formula

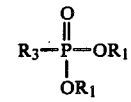

wherein $R_3$ is $C_1$–$C_{10}$alkyl and $R_1$ is $C_1$–$C_4$alkyl, with 1 mole of a metal $X^n$ selected from groups Ia, IIa, IIIa, IVa and VIII of the Periodic Table.

* * * * *